United States Patent
Hsu et al.

(10) Patent No.: US 9,687,198 B2
(45) Date of Patent: Jun. 27, 2017

(54) METHOD FOR DATA OSCILLATOR DETECTION USING FRICTIONALLY DAMPED HARMONIC OSCILLATORS

(75) Inventors: David Ambrose Hsu, Middleton, WI (US); Murielle Aline Hsu, Middleton, WI (US); Gregory A Worrell, Rochester, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1872 days.

(21) Appl. No.: 12/903,001

(22) Filed: Oct. 12, 2010

(65) Prior Publication Data

US 2012/0089004 A1 Apr. 12, 2012

(51) Int. Cl.
*A61B 5/02* (2006.01)
*A61B 5/00* (2006.01)
*A61B 5/04* (2006.01)
*G10L 25/48* (2013.01)

(52) U.S. Cl.
CPC .......... *A61B 5/726* (2013.01); *A61B 5/04001* (2013.01); *A61B 5/04014* (2013.01); *A61B 5/4094* (2013.01); *G10L 25/48* (2013.01)

(58) Field of Classification Search
CPC .............................. A61B 5/0476; A61B 5/0482
USPC .................................................. 600/544–545
See application file for complete search history.

(56) References Cited

PUBLICATIONS

"An algorithm for detecting oscillatory behavior in discretized data: the damped-oscillator oscillator detector" by Hsu et al., 2007—http://arxiv.org/abs/0708.1341.*
Time-frequency analysis using damped-oscillator pseudo-wavelets: Application to electrophysiological recordings by Hsu et al., Published online Oct. 7, 2010, doi: 10.1016/j.jneumeth.2010.09.019.*
Farge, Wavelet Transforms and their Applications to Turbulence, Annu. Rev. Fluid Mech., 1992, 24:395-457.
Hou, et al., A System Identification Technique Using Pseudo-Wavelets, Journal of Intelligent Material Systems and Structures, 2001, 12:681-687.
Hsu, et al., An Algorithm for Detecting Oscillatory Behavior in Discretized Data: the Damped-Oscillator Oscillator Detector, 2007, arXiv:0708.1341v1 [q-bio.QM].
Mazilu, et al., Wavelet Transformations for Ultrashort Pulse Characterization, The 15th Annual Meeting of the IEEE Lasers and Electro-Optics Society, 2002, pp. 592-593.
Qiu, et al., Pseudo-Wavelet Analysis of Turbulence Patterns in Three Vegetation Layers, Boundary-Layer Meteorology, 1995, 72:177-204.

(Continued)

*Primary Examiner* — Patricia Mallari
*Assistant Examiner* — Vasuda Ramachandran
(74) *Attorney, Agent, or Firm* — Quarles & Brady, LLP (57) ABSTRACT

A system and method for time-frequency analysis in which acquired signals are modeled as frictionally damped harmonic oscillators having a friction factor that is not a free parameter are provided. The friction factor is selected as a function of the frequency value of the associated oscillator, such that an increase in both temporal and spectral resolution are provided over existing time-frequency analysis methods. The friction factor is also selected to define a spectral band, within which the given oscillator can detect data oscillations. The properly selected friction factor thereby provides the analysis over a broad spectral range that can span many orders of magnitude.

20 Claims, 3 Drawing Sheets

(56) References Cited

PUBLICATIONS

Szu, et al., Causal Analytical Wavelet Transform, Optical Engineering, 1992, 31(9):1825-1829.
Unser, et al., A Review of Wavelets in Biomedical Applications, Proceedings of the IEEE, 1996, 84(4):626-638.
Vazquez, et al., Wavelet Transforms for Optical Pulse Analysis, J. Opt. Soc. Am. A, 2005, 22(12):2890-2899.
Hsu, et al., A new method for detecting periodicities in the neuronal spike train: the damped-oscillator periodicity detector, 60th Annual Meeting of the American Academy of Neurology, Apr. 2008.

* cited by examiner

METHOD FOR DATA OSCILLATOR DETECTION USING FRICTIONALLY DAMPED HARMONIC OSCILLATORS

STATEMENT REGARDING FEDERALLY SPONSORED RESEARCH

This invention was made with government support under RR025012 awarded by the National Institutes of Health. The government has certain rights in the invention.

FIELD OF THE INVENTION

The field of the invention is systems and methods for time-frequency analysis. More particularly, the invention relates to systems and methods for detecting and analyzing oscillations in acquired signals, such as electrophysiological signals indicative of neuronal and other bioelectrical activity.

BACKGROUND OF THE INVENTION

Time-frequency analysis involves monitoring the changes in the frequency spectrum of a system over time. The analysis is of importance in a wide variety of fields of science and engineering. The old work-horse of frequency analysis, the fast Fourier transform ("FFT"), can be utilized in time-frequency analysis by segmenting data into time windows. By monitoring changes in the power spectrum in each time window, the presence or absence of activity at certain frequencies within that time window can be determined. The segmentation process, however, introduces artifacts and precludes finer time resolution within the time windows. To address this problem, several refinements of the FFT approach have been proposed. These refinements, however, are all somewhat labor intensive, requiring judgments to be made about time window sizes and windowing functions, which may be different for different frequency ranges.

Over the last twenty years, wavelet transforms have become an important new tool for performing time-frequency analysis. A wavelet includes an oscillatory waveform that has a fairly well-defined frequency, and which exists only for a brief period of time. By convolving time series data with a suitably chosen wavelet, a determination of whether an oscillation of a certain frequency is present at a certain interval in time can be made, and in a manner that is more convenient and less susceptible to artifact than time windowed FFT. There are many kinds of wavelets and many applications of wavelet transforms to electroencephalography ("EEG") analysis.

A defining property of wavelets is the admissibility criterion, a consequence of which is that the mean of the wavelet when averaged over all time must equal zero. This criterion ensures that a stable inverse transform exists. A stable inverse transform is important for reliable signal transmission and reconstruction. However, in many fields of science and engineering, signal reconstruction is not the desired end result; rather, it may only be desirable to detect whether oscillations of certain frequencies appear, at what times they appear, and for what duration of time they exist. For example, in the brain, it is known that oscillations in the theta (4-8 Hz) and gamma (30-100 Hz) ranges are associated with cognitive activity. Oscillations from these two frequency ranges are sometimes phase-coupled, such that the faster gamma frequencies ride entirely on the crests, or troughs, of slower theta rhythms. Of increasing clinical interest are high frequency oscillations ("HFOs") in the range of 200-500 Hz. These oscillations tend to occur more frequently in brain regions that are epileptogenic, and so may be useful as a marker for tissue that should be surgically resected in patients with refractory epilepsy. For these applications, it might be desirable to relax the admissibility criterion. Relaxing the admissibility criterion results in a wide class of waveforms called pseudo-wavelets, or quasi-wavelets, which have found application in the study of turbulence and other complex phenomena.

One such pseudo-wavelet was previously described for discretized data applications by D. Hsu, et al., in "An Algorithm for Detecting Oscillatory Behavior in Discretized Data: the Damped-Oscillator Oscillator Detector," 2007; arXiv:0708.1341v1 [q-bio.QM]. The pseudo-wavelet discussed by Hsu, et al., corresponded to using a mathematical model of a frictionally damped harmonic oscillator to detect data oscillations of the same frequency as the damped harmonic oscillator. While this pseudo-wavelet included a friction factor to damp the mathematical oscillator, the friction factor was used as a free parameter to control noise in the time-frequency analysis process. Thus, while the pseudo-wavelet discussed in Hsu, et al., provided temporal resolution benefits, it was still constrained by existing spectral resolution limitations.

It would therefore be desirable to provide a system and method for time-frequency analysis in which higher temporal resolution than that achievable with Fourier analysis is achievable, while simultaneously increasing the achievable spectral resolution of the analysis. Preferably, such a dual increase in temporal and spectral resolution would be provided without an undue increase in computational burden.

SUMMARY OF THE INVENTION

The present invention overcomes the aforementioned drawbacks by providing a system and method for time-frequency analysis in which acquired signals are modeled as frictionally damped harmonic oscillators having a friction factor that is not a free parameter, but a specific parameter selected in a manner that provides both an increase in temporal and spectral resolution over existing time-frequency analysis methods. Moreover, with the appropriate selection of the friction factor, the number of oscillators required to perform time-frequency analysis over a broad spectral range can be significantly reduced, thereby providing time-frequency analysis without an undue increase in computational burden. To further reduce the computational burden of time-frequency analyses, a wavefunction formalism is provided for the pseudo-wavelet. Such a mathematical formalism further provides application of the pseudo-wavelet to non-discretized data.

It is an aspect of the invention to provide a method for the time-frequency analysis of acquired signals, such as electrophysiological signals acquired from a subject. Such electrophysiological signals can include those signals indicative of neuronal or other bioelectrical activity. The provided time-frequency analysis is also applicable to other signals, such as those indicative of speech. The provided method acquires signals and generates a selected number of oscillators for a respective selected number of frequency values. Each oscillator models the acquired signals as damped harmonic oscillators that are frictionally damped by a friction factor. The friction factor is selected for each oscillator to balance trade-offs between temporal and spectral resolution. For each oscillator, a corresponding wavefunction is calculated, from which a spectral density metric is calculated. For example, the spectral density metric may be a power metric, such as a data power indicative of energy changes in the oscillators that result from a data driving force. A report indicating the presence of oscillations in the acquired signals at the frequency values throughout a desired frequency band is produced. The report includes information related to the calculated spectral density metrics.

It is another aspect of the invention to provide a method measuring correlations between oscillators having different frequency values, or that are located at different locations in space. For example, correlations between oscillators in electroencephalography signals at the theta and gamma frequency ranges can be measured. Correlation information is calculated using a power metric such as the data power.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

The present invention provides a so-called damped-oscillator oscillator detector ("DOOD") pseudo-wavelet for detecting oscillations in an acquired signal, such as an electrophysiological signal indicative of neuronal or other bioelectrical activity. Generally, the DOOD pseudo-wavelet provides a mathematical model for oscillating signals that generates mathematical oscillators that are analogous to mechanical oscillators. One approach to generating the DOOD oscillators is to generate a set of mathematical harmonic oscillators, each of which has its own natural frequency of oscillation. Then, a time series of data, such as an electrophysiological signal, serves as a driving force that acts upon each mathematical harmonic oscillator. Thus, starting with the mathematical oscillators all at rest, the time series data will drive activity in the mathematical oscillators. If there is an oscillation in the data (a "data oscillator") that is substantially resonant with one of the generated mathematical oscillators, then that mathematical oscillator will steadily gain in energy. That mathematical oscillator will continue to gain in energy as long as the data oscillator remains on. If the data oscillator is turned off, the energy of the mathematical oscillator will plateau. If the data oscillator is turned back on again, the mathematical oscillator will either gain or lose energy, depending on whether the data oscillator is in-phase or out-of-phase with the mathematical oscillator. Sudden increases or decreases in energy are both markers of a resonant oscillation in the data. Therefore, the time rate of change of the energy of each mathematical oscillator, that is, its power, is monitored.

Time resolution is improved in this scheme by allowing friction to act on the mathematical oscillators. Friction induces the mathematical oscillators to approach a steady state. The steady state will be different depending on whether or not there is resonant driving of the mathematical oscillators by data oscillators. The higher the friction, the faster the mathematical oscillator approaches steady state and the better the time resolution for detecting when data oscillators turn on and off.

By way of example, let $x_{data}(t)$ represent the voltage recorded by a given electrode at time, t, and let $v_{data}(t)$ denote its first time derivative. For ease of notation, the succeeding discussion considers time series data from one electrode; however, the generalization to many electrodes is mathematically straightforward. Let h(t) denote the driving force of the mathematical oscillators, which can be selected as either $x_{data}(t)$ or $v_{data}(t)$. If $h(t)=x_{data}(t)$, the algorithm is referred to as X-DOOD. If $h(t)=v_{data}(t)$, the algorithm is referred to as V-DOOD. Here "X" is meant to suggest a coordinate, and "V," a velocity.

The time series in $x_{data}(t)$ is more sensitive to low frequency activity, while that in $v_{data}(t)$ is more sensitive to higher frequency activity. The reason that $v_{data}(t)$ is more sensitive to higher frequency activity is because the instantaneous time derivative of a sinusoid is equal to the frequency of oscillation of the sinusoid times the amplitude of the sinusoid. For example, if $x_{data}(t)=A\cdot\sin(\omega t)$, then $v_{data}(t)=A\cdot\omega\cdot\cos(\omega t)$. The extra factor of $\omega$ in $v_{data}(t)$ magnifies the effect of high frequency oscillations in $v_{data}(t)$ relative to that of low frequency oscillations. Conversely, for very small $\omega$, the extra factor of $\omega$ in $v_{data}(t)$ reduces the effect of low frequency oscillations in $v_{data}(t)$ relative to that of high frequency oscillations. Thus, it is contemplated that V-DOOD is more sensitive to high frequency oscillations while X-DOOD is more sensitive to low frequency oscillations. In general, it may be desirable to implement both X-DOOD and V-DOOD when performing time-frequency analysis in order to explore both low frequency and high frequency structure.

Let x(n,t) represent the coordinate of the $n^{th}$ mathematical oscillator, v(n,t) its velocity, M(n) its mass, g(n) its friction factor, and $\omega_0(n)$ its radial frequency, with n=1 ... $N_f$, where $N_f$ is the total number of mathematical oscillators to be generated. For convenience, the masses can be set equal to one; that is, M(n)=1 for all n. The equation of motion for the $n^{th}$ mathematical oscillator is then:

$$\frac{\partial^2 x(n,t)}{\partial t^2} = h(t) - \omega_0^2(n)x(n,t) - 2g(n)v(n,t); \quad (1)$$

The simplest non-transient solution for Eqn. (1) can be written in terms of a complex wavefunction, $\psi(n,t)$, as:

$$\psi(n,t) = \int_0^t h(t') \cdot e^{-(g(n)-i\omega(n))(t-t')} dt'; \quad (2)$$

where $\omega(n)^2 = \omega_0^2(n) - g^2(n)$. Taking $\psi_R(n,t)$ and $\psi_I(n,t)$ to be the real and imaginary parts of $\psi(n,t)$, respectively, yields:

$$x(n, t) = \frac{1}{\omega(n)} \cdot \psi_I(n, t); \quad (3)$$

$$v(n, t) = \psi_R(n, t) - \frac{g(n)}{\omega(n)} \cdot \psi_I(n, t). \quad (4)$$

The wavefunction, $\psi(n,t)$, can be calculated rapidly using a recursion relationship. To derive this relationship, take one incremental time step, $\delta t$:

$$\psi(n, t + \delta t) = \int_0^{t+\delta t} h(t') \cdot e^{-(g(n)-i\omega(n))(t+\delta t-t')} dt'; \quad (5)$$

which, for a significantly small time step, $\delta t$, can be rewritten as:

$$\psi(n,t+\delta t) = h(t+\delta t)\delta t + e^{-(g(n)-i\omega(n))\delta t}\psi(n,t) \quad (6)$$

Using Eqn. (6) and given $h(t+\delta t)$ and $\psi(n,t)$, $\psi(n,t+\delta t)$ can be calculated rapidly without needing to recalculate $\psi(n,t)$ or to keep track of $h(t)$ from prior time steps. It is noted that the exponential factor in Eqn. (6) has to be calculated only once before taking the first time step, thereby saving a certain amount of computational cost. Once $\psi(n,t+\delta t)$ is calculated, $x(n,t+\delta t)$ and $v(n,t+\delta T)$ can be readily calculated using Eqns. (3) and (4).

The instantaneous energy of the $n^{th}$ mathematical oscillator has terms that involve the friction factor and terms that are independent of the friction. Since it is desirable to measure changes in the energy due to coupling to $h(t)$, the terms that depend on the friction factor can be typically dropped wherever they arise. The instantaneous energy of the $n^{th}$ frictionless harmonic oscillator is given by:

$$E_0(n) = \frac{1}{2}v^2(n, t) + \frac{1}{2}\omega_0^2(n)x^2(n). \quad (7)$$

The first term is the kinetic energy term, and the second term is the potential energy term. Taking the time derivative of Eqn (7) and inserting Eq. (1), the time rate of change of the instantaneous energy, that is, the instantaneous power is determined and given by:

$$\frac{\partial}{\partial t}E_0(n) = v(n, t)(h(t) - 2g(n)v(n, t)). \quad (8)$$

The term in Eqn. (8) containing $g(n)$ is a term due to friction, which may be ignored. The term containing $h(t)$ is the power due to the data driving force. This data driving term is selected as a power metric that serves as a measure of spectral density. To emphasize that this measure is that part of the total power due only to the data driving force, this power metric is referred to as the "data power." The data power is, therefore, written as:

$$S(n,t)=v(n,t)h(t) \quad (9).$$

The data power, $S(n,t)$, is sensitive to a broad range of frequencies. Furthermore, a related measure, the square of the data power, $S^2(n,t)$, is especially sensitive to low frequency structures.

In comparison, the more traditional wavelet and pseudo-wavelet approaches identify the total energy of the wavefunction, $\psi(n,t)$, as the spectral density, which is given as:

$$E(n,t)=|\psi(n,t)|^2 \quad (10).$$

In the absence of friction, the total energy, $E(n,t)$, plateaus when there are no active data oscillators. In the presence of friction, the total energy decays back to baseline with a rate given by the friction constant, $g(n)$, when the data oscillators are turned off. One might imagine looking at the total power, given by $\partial E(n,t)/\partial t$. This quantity drops back to baseline faster than the total energy, but it represents the total power and contains extraneous terms, such as the time rate of change of the energy due to friction, i.e., the second term in Eqn (8). Therefore, neither $E(n,t)$, nor $\partial E(n,t)/\partial t$, is as sensitive to state changes in the data oscillator as is $S(n,t)$. In some instances, the data power, $S(n,t)$, can show a sudden drop almost immediately after a data oscillator is turned off, within one period of the resonant frequency. Although the data power, $S(n,t)$, is still subject to the uncertainty principle, temporal resolution is typically much better with $S(n,t)$ than with $E(n,t)$. Thus, the data power, $S(n,t)$, provides a spectral density metric with superior temporal resolution characteristics relative to currently used metrics, including total energy, $E(n,t)$, and the time rate of change of the total energy, $\partial E(n,t)/\partial t$.

The friction factor, $g(n)$, can be used to sharpen the time resolution of the data power spectral density, $S(n,t)$. If a data oscillator turns on, drives up the spectral power to a new level, and then turns off, the friction factor will bring the data power spectral density back down to baseline on a time scale of $1/g(n)$. Thus, larger friction factors will bring down the spectral power faster, thereby giving better time resolution as to when the data oscillator turned off. However, larger friction factors will also cause broadening of the spectral peak. This manifestation of the uncertainty principle is expected and unavoidable. For example, if one inserts a pure sinusoid for $h(t)$ in Eqn. (2), one finds a Lorentzian line shape with a peak at the frequency of the sinusoid used for $h(t)$, and a half-width-at-half maximum ("HWHM") given by $g(n)$. The larger $g(n)$ is, the wider the Lorentzian peak becomes.

In light of these considerations, when choosing $g(n)$, a trade-off between better time resolution or better frequency resolution is confronted. Note from Eqn. (2) that if $g(n)=0$ is selected for all n, then, essentially, the finite Fourier transform is recovered to within a phase factor. For best time resolution, $g(n)$ may be chosen to be as large as possible, but no larger than the frequency value, $f(n)$, of the oscillator because it does not make sense to try to obtain better time resolution than the time period of the oscillation itself. For better frequency coverage that avoids any gaps in a desired frequency range, neighboring oscillators should be considered.

For example, if the frequency values, $f(n)$, are selected to lie on a conventional linear grid with:

$$f(n+1)=f(n)+\delta f \quad (11);$$

then it is most reasonable to select the friction factors as:

$$g(n)=2\pi \cdot \delta f \quad (12);$$

so that the spectral bandwidths of neighboring mathematical oscillators overlap, leaving no gap between. In such an instance, the absolute frequency resolution is given by $\delta f$, while the relative frequency resolution is given by:

$$\frac{g(n)}{\omega(n)} = \frac{\delta f}{f(n)}. \quad (13)$$

Note that in such an instance, the relative frequency resolution is proportional to 1/n; that is to say, the relative spectral bandwidth of each mathematical oscillator decreases for higher frequency oscillators.

Rather than setting the absolute frequency resolution constant for every mathematical oscillator, the relative frequency resolution should be set as a constant. For example, a grid constant, $g_0$, can be selected as:

$$g_0 = \frac{f(n+1) - f(n)}{f(n)}; \tag{14}$$

where the grid constant, $g_0$, is a small positive number that is the same for each mathematical oscillator. It is noted that smaller values of $g_0$ give better frequency resolution, but poorer time resolution. Such a choice then implies that the frequency grid is no longer linear, but geometric. That is to say, Eqn. (14) implies that the frequency values are selected in accordance with:

$$f(n+1) = f(n) \cdot (1+g_0) \tag{15}.$$

When the frequency range that needs to be spanned for a given problem is small, say on the order of 1-2 orders of magnitude, then it does not matter as much whether a linear or geometric frequency grid is selected. However, when the frequency range that needs to be spanned is on the order of three or more orders of magnitude, then computational economy suggests that one should adopt a geometric frequency grid. In this way, one can span the greatest frequency range with the smallest number of mathematical oscillators, while still maintaining the same relative spectral resolution of each mathematical oscillator.

By way of example, a geometric frequency grid may be employed when performing time-frequency analysis over a broad spectral range, such as 0.5-6000 Hz. In such an example:

$$f(n) = f(n-1) \cdot (1+g_0), \text{ with } f(1) = 0.5 \text{ Hz};$$

$$g_0 = 0.02; \text{ and}$$

$$g(n) = 2\pi \cdot g_0 \cdot f(n).$$

Using this selected geometric frequency grid, the spectral range of 0.5-6000 Hz can be spanned using only 476 mathematical oscillators. In comparison, if a linear frequency grid with $\delta f = g(n) = 1$ Hz is utilized, upwards of 6000 frequency points would be required to span the same range as with the aforementioned geometric frequency grid.

The sampling rate, $f_S$, of the raw data places an upper limit on the highest frequency oscillator that can be reliably calculated because, if there is an oscillation in the data that is of the same frequency or higher, then it will be artifactually "folded" into the dynamics of oscillators of somewhat lower frequency. This phenomenon, known as aliasing, applies equally to FFT and to the DOOD pseudo-wavelet. It is advisable, then, to consider using oscillators of frequency values no higher than $f_S/2$ for this reason.

For every pair of values for $x(n,t)$ and $v(n,t)$, calculated via Eqns. (3)-(4), an instantaneous phase, $\theta(n,t) = \omega(n)t + \delta(n)$, can be defined via:

$$x(n,t) = A \cdot \sin(\theta(n,t)) \tag{16};$$

$$v(n,t) = A \cdot \omega \cdot \cos(\theta(n,t)) \tag{17};$$

and $$\theta(n, t) = \arctan\left(\frac{\omega(n) \cdot x(n, t)}{v(n, t)}\right). \tag{18}$$

Since the spectral density of interest is the data power, a variety of correlation functions from the data power spectral density can be produced. One such correlation function, the pair correlation function, is defined as:

$$C(m, n; t) = \langle S(m, t)S(n, 0)\rangle \equiv \frac{1}{N_t}\sum_{k=1}^{N_t} S(m, t+k\delta t)S(n, k\delta t). \tag{19}$$

To extract phase information, it is desirable not to introduce phase shifts through the sign of the data power. This kind of artifact is preventable by squaring the data power before taking the time average:

$$C_C(m, n; t) = \langle S^2(m, t)S^2(n, 0)\cos\theta(n, 0)\rangle; \tag{20}$$

$$C_S(m, n; t) = \langle S^2(m, t)S^2(n, 0)\sin\theta(n, 0)\rangle; \tag{21}$$

$$\theta_0(m, n) = \arctan\left(\frac{C_S(m, n; 0)}{C_C(m, n; 0)}\right); \tag{22}$$

$$\sigma_0(m, n) = \sqrt{C_C^2(m, n; 0) + C_S^2(m, n; 0)}. \tag{23}$$

Equations (20)-(23) can be used to check whether the phase of the $n^{th}$ oscillator modifies the data power amplitude of the $m^{th}$ oscillator, where the $n^{th}$ and $m^{th}$ oscillators have different frequency values, but may be spectrally adjacent. If the $m^{th}$ oscillator tends to be more activated at a particular phase of the $n^{th}$ oscillator, then $\sigma_0(m,n)$ will be relatively larger for that pair of (m,n), and $\theta_0(m,n)$ will give the relative phase of the $n^{th}$ oscillator during which the square magnitude of the data power of the $m^{th}$ oscillator is largest.

Figure 1:
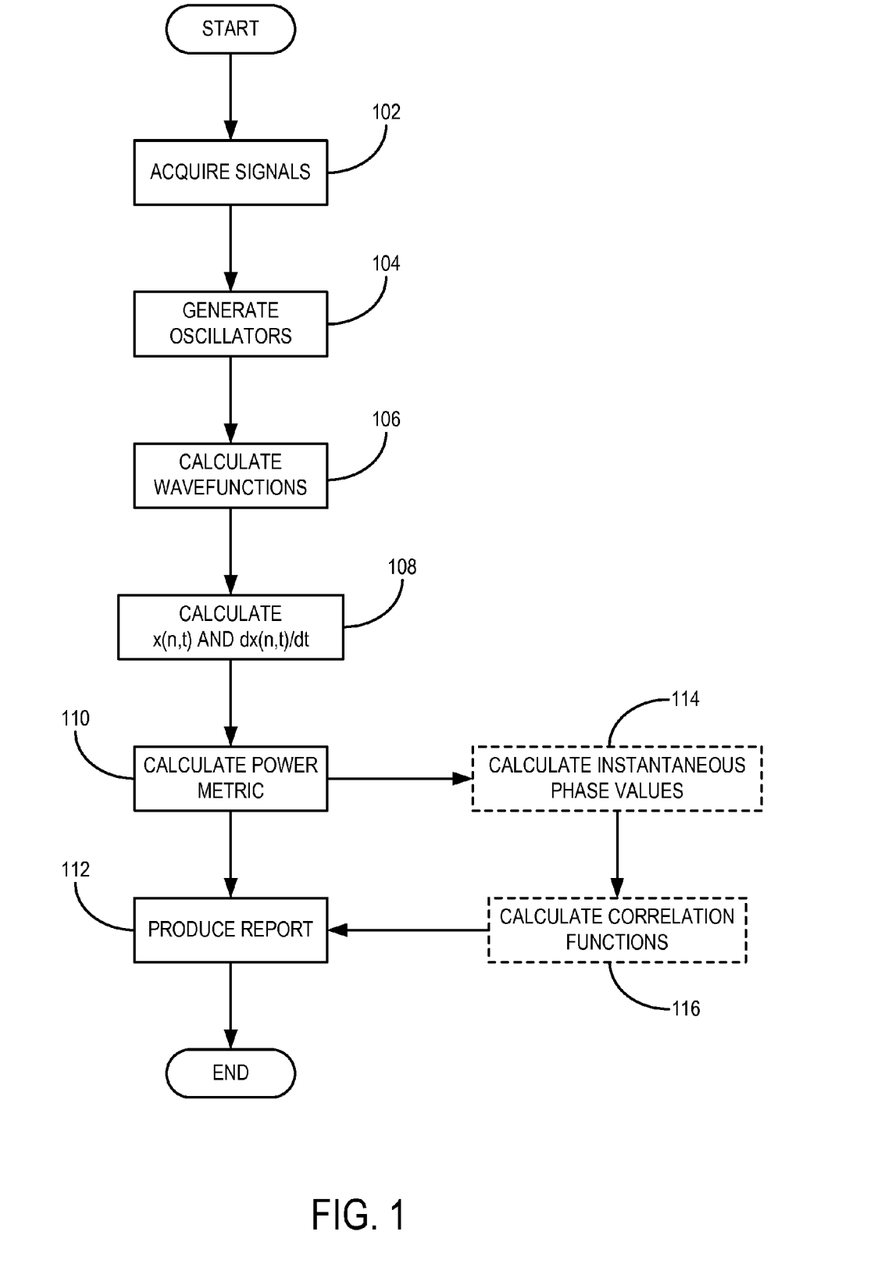
FIG. 1 is a flowchart setting forth the steps of an exemplary method for analyzing an electrophysiological signal using a damped-oscillator oscillator detector pseudo-wavelet.

With the foregoing explanation of concepts related to the application of the DOOD pseudo-wavelet to the detection of oscillations in a given signal in place, referring now to FIG. 1, a flowchart setting forth the steps of an exemplary method for analyzing a particular signal including oscillations, in this case, electrophysiological signals, such as electroencephalography ("EEG") signals, is illustrated. As applied to EEG signals, the DOOD method models the EEG signals as damped harmonic oscillators being affected by a selected friction factor that forms a part of the DOOD pseudo-wavelet. Particularly, the friction factor is selected to provide a spectral detection band centered about a given frequency value, such that fewer oscillators are required to provide detection coverage of a desired frequency range. The friction factor also provides an increase in temporal resolution to the detection process. In this manner, time-frequency analysis can be performed over a broad spectral range with high temporal resolution. It should be appreciated that while the present invention is described with respect to the analysis of electrophysiological signals, the time-frequency analysis method is also applicable to other applications, such as voice recognition, in which it is desirable to provide high temporal resolution over a broad range of frequency values.

The analysis method begins with the acquisition of electrophysiological signals from a subject, as indicated at step 102. For example, the electrophysiological signals are indicative of neuronal activity and are acquired by an EEG system or a deep brain stimulation system that is configured to measure neuronal activity in addition to supplying electrical stimulus therapy. A desired number of oscillators are generated, as indicated at step 104. As discussed above in detail, each oscillator models the acquired signals as a damped harmonic oscillator with a given frequency value and a given friction factor. Thus, when generating each oscillator, a friction factor is selected. The choice of friction factor is made while balancing trade-offs in temporal and spectral resolution. For example, to improve temporal resolution the friction factor is selected to be as large as possible while being smaller than the frequency value of the oscillator. That is:

$$g(n) < f(n) \qquad (24).$$

To provide a spectral resolution capable of covering a broad frequency range that spans many orders of magnitude, for example three of more orders of magnitude, a geometric grid spacing is used between oscillators. That is:

$$f(n+1) = f(n) \cdot (1+g_0) \text{ with } g_0 > 0 \qquad (25).$$

In such an instance, it is desirable to match the friction factor to the chosen frequency spacing. For example, the friction factor is selected as:

$$g(n) = f(n) \cdot \log(1+g_0) \qquad (26);$$

or, for $g_0 \ll 1$, $$g(n) = g_0 f(n) \qquad (27).$$

It is noted that when a nonlinear frequency spacing between oscillators is employed, conventional Fourier analysis techniques are inapplicable. That is, Fourier analysis techniques, such as those that rely on the fast Fourier transform ("FFT"), require a uniform, linear spacing between data points in order to properly operate on the data samples and to accurately identify the presence of oscillations at the desired frequency values.

After the desired oscillators have been generated, a wavefunction is calculated for each oscillator in accordance with Eqn. (6), as indicated at step 106. Each wavefunction is recursively calculated using Eqn. (6) given initial values for $h(t+\delta t)$ and $\psi(n,t)$. The initial value of $\psi(n,t)$ may, for example, be set as zero; however, other alternatives will be appreciated by those skilled in the art. The calculated wavefunctions are then utilized to calculate $x(n,t)$ and $v(n,t)$ for each respective oscillator, as indicated at step 108. For example, $x(n,t)$ is calculated in accordance with Eqn. (3), and $v(n,t)$ is calculated in accordance with (4). Having calculated $x(n,t)$ and $v(n,t)$ for each oscillator, a spectral density metric, such as a power metric, is calculated next, as indicated at step 110. While the total energy, $E(n,t)$, and time rate of change of the total energy, $\partial E(n,t)/\partial t$, can be calculated as the spectral density metric, it is desirable to calculate the data power in accordance with Eqn. (9). Moreover, in some applications, such as those in which low frequency structures are anticipated, the square of the data power, $S^2(n,t)$, may be calculated as the spectral density metric. The data power provides a spectral density measure that has a higher temporal resolution than both $E(n,t)$ and $\partial E(n,t)/\partial t$, thereby providing an improved time-frequency analysis metric. It is noted that it may not be desirable to determine the spectral density metric at every instant in time. For instance, it may be desirable to determine the spectral density metric only over a selected time interval, $\Delta t$. In such an instance, the spectral density metric can be temporally averaged over consecutive time intervals, each of a duration $\Delta t$, and written out as output at the termination of each such time interval.

Following the calculation of the spectral density metric, a report is generated, as indicated at step 112. By way of example, the report can include providing a visual display to a user, the display indicating the presence of oscillations in the acquired electrophysiological signals at certain frequency values, as identified by the calculated spectral density metric.

Optionally, the instantaneous phase of each generated oscillator is calculated, as indicated at step 114. This instantaneous phase information is utilized to determine correlations between oscillators having different frequencies or that are located at different points in space, as indicated at step 116. This correlation information is conveyed, for example, via correlation functions calculated using the data power, $S(n,t)$. Exemplary correlation functions include the pair correlation functions provided, generally, in Eqns. (19)-(23). This correlation information is utilized to assess whether coupling between oscillators is occurring. For example, the correlation information can be used to assess whether theta oscillations are coupled to higher frequency gamma oscillations. Information related to such a coupling is useful for recognizing patterns of seizure in epilepsy. It is contemplated that this information can be utilized to identify the onset of seizure such that an interventional electrical stimulus can be provided by way of a deep brain stimulation system to suppress the seizure event. For instance, if a seizure pattern is recognized as including a particular theta oscillation coupled to a number of gamma oscillations, in a specific spatial distribution, then it is contemplated that an electrical stimulation that mimics the theta-gamma temporal pattern, but that randomizes the spatial pattern, can be provided to the patient in order to disrupt the seizure. Such a pattern of stimulation may break seizures and, if applied repeatedly, may help "erase" the seizure pattern from the brain. Such methods of using temporal and spatial distributions of oscillations to design electrical stimulation therapies are described, for example, in co-pending U.S. patent application Ser. No. 12/426,430, which is herein incorporated by reference in its entirety. Other uses for this correlation information include supplementing presurgical plans for resection of seizure prone regions of the brain, and assessing drug toxicity for both clinical drug trials and a patient-by-patient evaluation. Like the spectral density metric, the instantaneous phase and correlation information can be included in the report produced at step 112.

Figure 2:
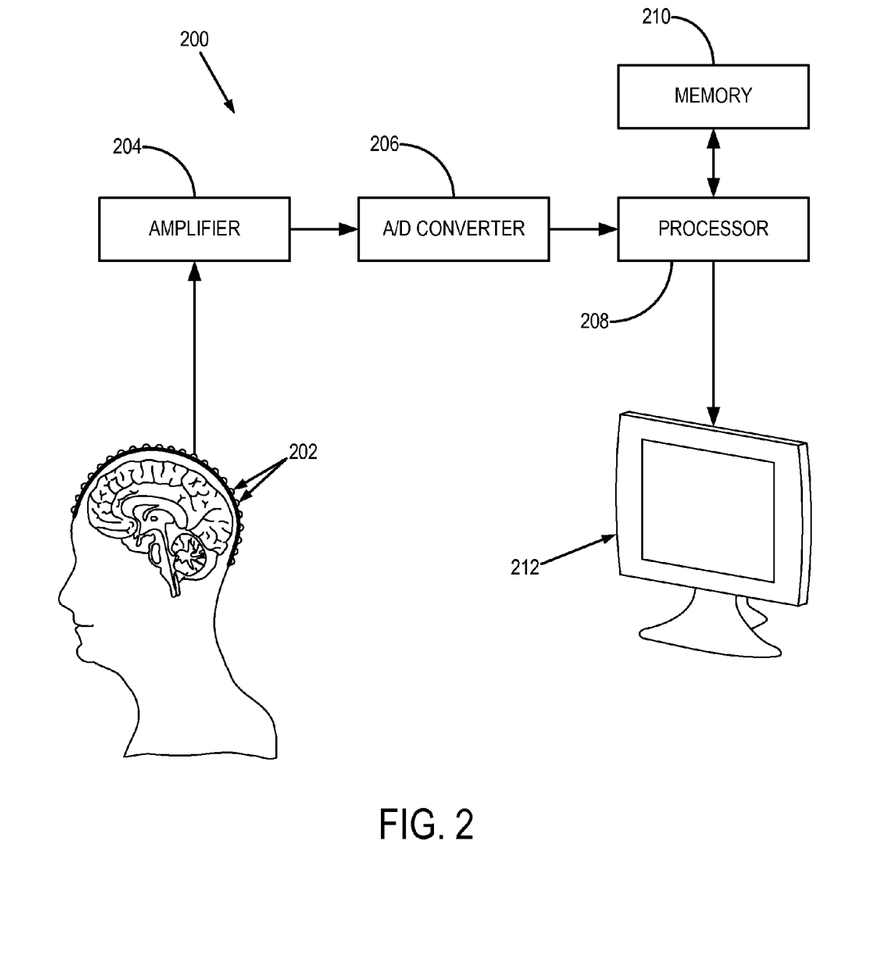
FIG. 2 is a block diagram of an exemplary electroencephalography system.

Referring now to FIG. 2, an exemplary electroencephalography ("EEG") system 200 for acquiring electrophysiological signals indicative of neuronal activity is illustrated. The electrophysiological signals measured and acquired with the EEG system 200 are acquired on a number of EEG electrodes 202, or sensors, for example, of the 10-20 international electrode placement system.

During measurement of neuronal activity with the EEG system, a continuous stream of voltage data representative of an electrophysiological signal is detected by the electrodes 202, which are coupled to the subject's scalp, and the acquired signals are sampled and digitized. Specifically, an amplifier 204 in communication with the electrodes 202 is used to amplify the acquired signals, after which the amplified signals are sent to an analog-to-digital ("A/D") converter 206 that converts the signals from analog to digital format. The acquired signals can also undergo additional preprocessing in order to remove artifacts, such as those due to data collection and physiological causes. The digital signals are sent to a processor 208 that processes the signals as described in detail above. The processor 208 is also configured to store the processed or unprocessed signals in a memory 210, and to display the signals on a display 212.

Figure 3:
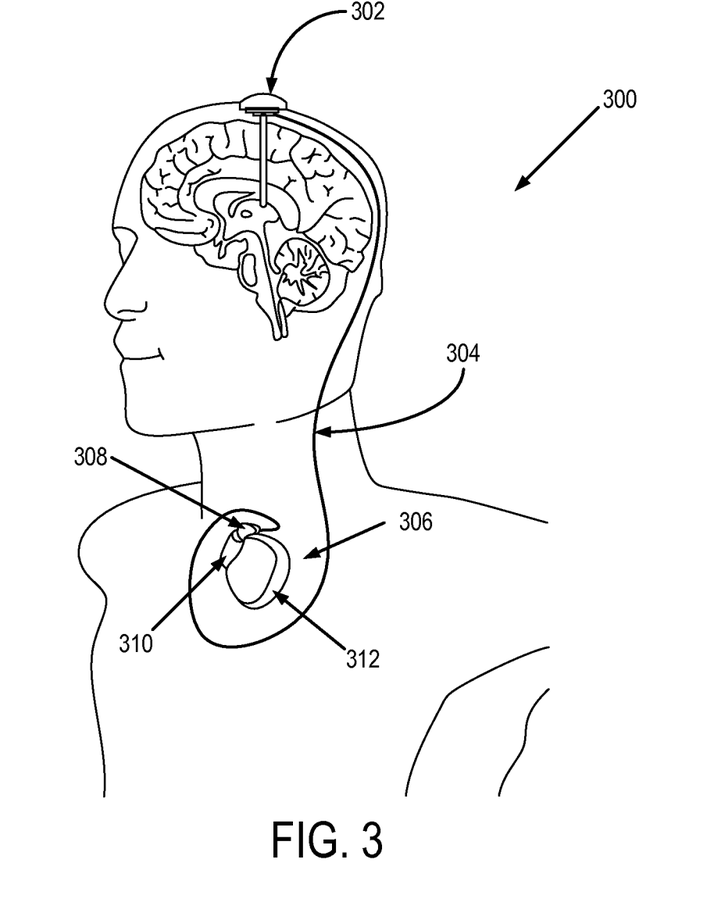
FIG. 3 is a pictorial representation of an exemplary deep brain stimulation system configured to acquire signals that measure neuronal activity and to deliver electrical stimulus therapy to a subject's brain.

Referring now to FIG. 3, the present invention can be implemented using a deep brain stimulation ("DBS") system 300 capable of recording neural activity and administering electrical stimulation to a target brain area to prevent anticipated pathological neural activity. An exemplary DBS system 300 includes an electrode probe 302 that is capable of both stimulating populations of neurons and measuring single-unit neuronal activity. The probe 302 is typically implanted in the subject and connected via an insulated lead 304 to a neurostimulator 306. It is contemplated that the lead 304 runs under the skin of the head, neck, and shoulder and that the neurostimulator 306 is implanted to sit inferior to the clavicle. The neurostimulator 306 includes a pulse generator 308, a controller 310, and a battery pack 312 configured to power the DBS system 300. The neurostimulator 306 can also include a memory to store measured neural activity data and models for implementation on the controller 310.

In operation, the DBS system 300 measures neuronal activity data by acquiring electrophysiological signals from the brain with the electrode probe 302. These electrophysiological signals are carried via lead 304 to the neurostimulator 306 where they are processed by the controller 310. The controller 310 analyzes the signals and identifies a corrective stimulation signal that will prevent anticipated pathological neural events. The selected stimulation signal is then generated by the pulse generator 308 and delivered via the lead 304 to the electrode probe 302, which administers the stimulation signal to the target area. Depending on the predicted neural activity, the stimulation signal may inhibit the neuron, excite the neuron, or do nothing.

The present invention has been described in terms of one or more preferred embodiments, and it should be appreciated that many equivalents, alternatives, variations, and modifications, aside from those expressly stated, are possible and within the scope of the invention.

We claim:

1. A computer-implemented method for analyzing electrophysiological signals acquired from a subject, the steps of the method comprising:
   a) acquiring electrophysiological signals from a subject using a device configured to measure bioelectrical activity;
   b) generating with a computer system, a selected number of oscillators for a respective selected number of frequency values, each of the selected oscillators modeling the acquired electrophysiological signals as damped harmonic oscillators that are damped by a friction factor selected by the computer system using the respective frequency value of the oscillator;
   c) calculating with the computer system, a wavefunction for each oscillator;
   d) calculating with the computer system, a spectral density metric for each of the selected oscillators using the associated calculated wavefunctions and the acquired electrophysiological signals;
   e) producing with the computer system, a report indicating a presence of oscillations in the acquired electrophysiological signals at frequency values throughout a desired frequency band using the calculated spectral density metrics; and
   f) outputting the report to a display device.

2. The method as recited in claim 1 in which the report produced in step e) further indicates a time at which oscillations occurred in the acquired electrophysiological signals and a duration of each oscillation that occurred.

3. The method as recited in claim 1 in which successive oscillators have frequency values that are nonlinearly spaced apart.

4. The method as recited in claim 3 in which the frequency values are selected by the computer system in accordance with $f(n)=f(n-1)\cdot(1+g_0)$ and the friction factors are selected by the computer system in accordance with at least one of $g(n)=f(n)\log(1+g_0)$ and $g(n)=g_0 f(n)$, wherein $f(n)$ is the frequency value for an $n^{th}$ oscillator, $f(n-1)$ is the frequency value for an $(n-1)^{th}$ oscillator, $g_0$ is a frequency grid constant, and $g(n)$ is the friction factor for the $n^{th}$ oscillator.

5. The method as recited in claim 1 in which the spectral density metric calculated in step d) is indicative of changes in energy of each of the selected oscillators, the changes in energy being due to a driving force of each of the selected oscillators.

6. The method as recited in claim 5 in which the driving force is at least one of the acquired electrophysiological signals and a first time derivative of the acquired electrophysiological signals.

7. The method as recited in claim 1 in which each of the selected oscillators includes a spectral band defined by the friction factor of each of the selected oscillators.

8. The method as recited in claim 1 in which the spectral density metric is at least one of a data power and a squared data power, and step d) includes calculating with the computer system, a first time derivative of the acquired electrophysiological signals for each of the selected oscillators using the associated calculated wavefunction.

9. The method as recited in claim 8 in which step d) further includes calculating the spectral density metric by multiplying the calculated first time derivative with at least one of the acquired electrophysiological signal and the calculated first time derivative.

10. The method as recited in claim 1 in which the electrophysiological signals are indicative of neuronal activity and are acquired using at least one of an electroencephalography system and a deep brain stimulation system.

11. The method as recited in claim 1 further comprising calculating with the computer system, a correlation between at least two or more of the selected oscillators using the calculated spectral density metric.

12. An apparatus configured to perform time-frequency analysis of a time series of data, the apparatus comprising:
   a user interface for selecting a frequency value
   a processor in communication with the user interface, configured to receive the selected frequency value and the selected friction factor, and configured to:
   (i) select a friction factor using the selected frequency value;
   (ii) generate, for the selected frequency value, an oscillator modeling the time series of data as a damped harmonic oscillator that is damped by the selected friction factor;
   (iii) calculate a wavefunction for the oscillator;
   (iv) calculate a power metric for the oscillator using the calculated wavefunction and the time series of data;
   (v) identify whether a data oscillation exists in the time series of data at the selected frequency value using the calculated power metric;
   (vi) repeat steps (i)-(v) using a plurality of different frequency values received from the user interface to generate a plurality of different oscillators for each of the received plurality of different frequency values;

(vii) produce a report using the calculated power metrics, the report indicating a presence of the identified data oscillations; and (viii) outputting the report to a display device.

13. The apparatus as recited in claim 12 in which the report produced in step (vi) further indicates a time at which each identified data oscillation occurred, and a duration of each identified data oscillation.

14. The apparatus as recited in claim 12 in which the plurality of different oscillators are nonlinearly spaced apart.

15. The apparatus as recited in claim 12 in which the processor is further configured to select the friction factor in step (i) in accordance with at least one of $g=g_0$, $g=f \cdot \log(1+g_0)$, and $g=g_0 f$, wherein g is the friction factor for the oscillator, f is the frequency value for the oscillator, and $g_0$ is a frequency grid constant.

16. The apparatus as recited in claim 12 in which the processor is further configured to calculate a correlation between at least two of the plurality of generated oscillators using the calculated power metric.

17. The apparatus as recited in claim 16 in which the correlation is a pair correlation calculated in accordance with:

$C(m,n;t) = \langle S(m,t)S(n,0) \rangle$ ; wherein $C(m,n;t)$ is the pair correlation between an $n^{th}$ and an $m^{th}$ generated oscillator;

$S(m,t)$ is the power metric for the $m^{th}$ generated oscillator at a time, t; and $S(n,0)$ is the power metric for the $n^{th}$ generated oscillator at a time t=0.

18. A computer-implemented method for analyzing a signal to determine frequency characteristics thereof, the steps of the method comprising:

a) selecting with a computer system, a plurality of frequency values throughout a desired frequency band;

b) selecting with the computer system, a friction factor for each selected frequency value using the respective selected frequency value;

c) generating with the computer system and for each selected frequency value and respective friction factor, an oscillator that models the signal as a damped harmonic oscillator that is damped by the friction factor;

d) calculating with the computer system, a wavefunction for each of the generated oscillators;

e) calculating with the computer system, a spectral density metric for each of the generated oscillators using the associated calculated wavefunction and the signal;

f) producing with the computer system, a report indicating a presence of oscillations in the signal at frequency values throughout the desired frequency band using the calculated spectral density metric; and e) outputting the report to a display device.

19. The method as recited in claim 18 in which the selected plurality of frequency values are non-uniformly spaced apart.

20. The method as recited in claim 19 in which the selected plurality of frequency values are spaced apart in accordance with a geometric grid spacing.

* * * * *